(12) United States Patent
Partain

(10) Patent No.: US 8,559,590 B2
(45) Date of Patent: Oct. 15, 2013

(54) IMAGING BREAST CANCEROUS LESIONS WITH MICROCALCIFICATIONS

(75) Inventor: Larry D. Partain, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 279 days.

(21) Appl. No.: 12/695,896

(22) Filed: Jan. 28, 2010

(65) Prior Publication Data

US 2011/0182402 A1    Jul. 28, 2011

(51) Int. Cl.
*A61B 6/03* (2006.01)
(52) U.S. Cl.
USPC .................................. 378/9; 378/21; 378/37
(58) Field of Classification Search
USPC ........................ 378/9, 37, 8, 21, 22
See application file for complete search history.

(56) References Cited

U.S. PATENT DOCUMENTS

| | | | | |
|---|---|---|---|---|
| 5,511,105 A * | 4/1996 | Knott | | 378/134 |
| 6,229,876 B1 * | 5/2001 | Enck et al. | | 378/136 |
| 6,463,122 B1 * | 10/2002 | Moore | | 378/65 |
| 2003/0076920 A1 * | 4/2003 | Shinno et al. | | 378/4 |
| 2003/0169847 A1 * | 9/2003 | Karellas et al. | | 378/98.3 |
| 2003/0235266 A1 * | 12/2003 | Gregerson et al. | | 378/4 |
| 2004/0258195 A1 * | 12/2004 | Hara | | 378/11 |
| 2005/0117694 A1 * | 6/2005 | Francke | | 378/4 |
| 2006/0222143 A1 * | 10/2006 | Du | | 378/11 |
| 2008/0101530 A1 * | 5/2008 | Ullberg et al. | | 378/4 |
| 2009/0080602 A1 * | 3/2009 | Brooks et al. | | 378/20 |
| 2009/0232275 A1 * | 9/2009 | Spartiotis et al. | | 378/40 |

FOREIGN PATENT DOCUMENTS

WO        2006119426 A2    11/2006

* cited by examiner

*Primary Examiner* — Glen Kao
(74) *Attorney, Agent, or Firm* — Houst Consulting

(57) ABSTRACT

A radiation system includes a first radiation source and a first detector positioned opposite to each other configured to image a body portion, and a second radiation source and a second detector positioned opposite to each other configured to image a region of interest in the body portion. The first radiation source has a first spot size and the first detector has a first pixel size. The second radiation source has a second spot size and the second detector has a second pixel size. The first spot size of the first radiation source may be different from the second spot size of the second radiation source, and/or the first pixel size of the first detector may be different from the second pixel size of the second detector.

5 Claims, 1 Drawing Sheet

IMAGING BREAST CANCEROUS LESIONS WITH MICROCALCIFICATIONS

BACKGROUND

This invention relates generally to radiation systems and methods and in particular to methods and apparatus for imaging patients' breasts with high resolution to identify cancerous lesions with microcalcifications.

Breast cancer is one of the most common cancers among women in the United States. Each year, about 200,000 American women are diagnosed to have breast cancer. One of eight women born today will be diagnosed with breast cancer at some time during their lifetime. For successful treatment of breast cancer, early detection and diagnosis are crucial. Conventional X-ray mammography has been shown a cost-effective tool for early detection of breast cancer. However, the predictive value and specificity of X-ray mammography are limited partly due to projecting a three-dimensional breast into a two-dimensional image. The minimum cancerous lesion size that can be detected by conventional X-ray mammography has been on the order of 10 mm in diameter, which is about 1000 times larger than a 1 mm cancerous lesion in volume. It is believed that a 1 mm cancerous lesion grows at an exponential growth rate that finally leads to a lesion with 10 mm size when the growth rate begins to decrease. It would be desirable to detect and monitor the growth of cancerous lesions at early stages.

FIG. 1 shows a conventional computed tomography (CT) machine for imaging patients' breasts. The machine includes a single C-arm with an X-ray imager attached at one side and an X-ray tube mounted at the opposite. In use the patient lies prone with a pendulant single breast to be imaged protruding through a hole in the support couch. The C-arm supporting the X-ray imager and X-ray tube rotates to provide cone beam CT image data sets or limited angle digital tomosynthesis data sets. The CT machine shown in FIG. 1 allows the breast tissue to be imaged without the need to flatten or compress the breast as in mammography. Confusion caused by superposition of soft tissue layers as in mammography may be avoided as the soft tissue layers can be decomposed into desired single cross-sectional image slices without the interference of features in layers before or after the particular image slice. However, the CT machine shown in FIG. 1 does not provide the spatial resolution to resolve microcalcifications, tiny calcium deposits inside the breast tissue which pattern has high correlation with cancer. Microcalcifications are used to diagnose about 50 percent of breast cancers and are found to accompany about 80 percent of actual breast cancers.

SUMMARY

The present invention provides a radiation system and method that is particularly useful in imaging breast cancerous lesions and microcalcifications in the breast tissue. In the provided radiation system and method, a radiation source with a high power output and a detector with a large active detection area can be used to rapidly acquire an image data set for a whole breast or a portion of the breast in a short period of time. The image data set is processed or reconstructed, and from a reconstructed image of the whole breast or a portion of the breast, some regions of interest (ROI) of reduced volume suspected of cancerous lesions may be identified. A radiation source with a small spot size and a detector with a small pixel size can be used to image the identified suspect ROI to acquire an additional image data set, which can then be processed, reconstructed, and analyzed with high spatial resolutions that are available from the small spot size and small pixel size systems. With the disclosed apparatus and method, microcalcifications in the breast tissue and small cancerous lesions of the size on the order of 10's of microns or down to microns can be detected while radiation doses to surrounding healthy tissue can be significantly minimized.

Accordingly, in one embodiment, a radiation system includes a first radiation source and a first detector positioned opposite to each other configured to image a body portion, and a second radiation source and a second detector positioned opposite to each other configured to image a region of interest in the body portion. The second radiation source and/or second detector may be movable in one or more directions relative to each other. The first radiation source and first detector may be fixedly positioned relative each other. The first radiation source, the first detector, the second radiation source, and the second detector may be rotatable about an axis such as an axis passing through the body portion.

The first radiation source may have a first spot size and the first detector a first pixel size. The second radiation source may have a second spot size and the second detector a second pixel size. In some embodiments, the first spot size of the first radiation source is different from the second spot size of the second radiation source, or the first pixel size of the first detector is different from the second pixel size of the second detector. In some embodiments, the first radiation source may have a spot size ranging from about 0.5 to 3 mm and the first detector may have a pixel size ranging from about 100 to 200 microns. The second radiation source may have a spot size ranging from 0.1 to 200 microns and the second detector may have a pixel size ranging from about 0.5 to 100 microns.

In one aspect the invention provides a radiation method including the following steps. A body portion is imaged to acquire a first image data set. A region of interest in the body portion is identified based on the first image data set. The region of interest is imaged to acquire a second image data set. The first image data set may be a cone beam CT image data set or a digital tomosynthesis image data set. The second image data set may be a single projection image, or a cone beam CT image data set or a digital tomosynthesis image data set.

The first image data set may be acquired using a first radiation source having a first spot size and a first detector having a first pixel size. The second image data set may be acquired using a second radiation source having a second spot size and a second detector having a second pixel size. The first spot size of the first radiation source may be different from the second spot size of the second radiation source, and/or the first pixel size of the first detector may be different from the second pixel size of the second detector.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION OF EXEMPLARY EMBODIMENTS

Various embodiments of radiation apparatuses and methods are described. It is to be understood that the invention is not limited to the particular embodiments described as such may, of course, vary. An aspect described in conjunction with a particular embodiment is not necessarily limited to that embodiment and can be practiced in any other embodiments. For instance, while various embodiments are described in connection with X-ray tubes and imagers, it will be appreciated that the invention can also be practiced in other electromagnetic apparatuses and modalities. The disclosed apparatus and method can be used not only in imaging a patient's breast but also in imaging and/or treating other body parts of human beings, animals, and any objects of interest. It is also to be understood that the terminology used herein is for the purpose of describing particular embodiments only, and is not intended to be limiting since the scope of the invention will be limited only by the appended claims, along with the full scope of equivalents to which such claims are entitled.

In addition, various embodiments are described with reference to the figures. It should be noted that the figures are not drawn to scale, and are only intended to facilitate the description of specific embodiments. They are not intended as an exhaustive description or as a limitation on the scope of the invention.

All technical and scientific terms used herein have the same meaning as commonly understood by one of ordinary skill in the art to which this invention belongs, unless defined otherwise. As used in the description and appended claims, the singular forms of "a," "an," and "the" include plural references unless the context clearly dictates otherwise.

Figure 1:
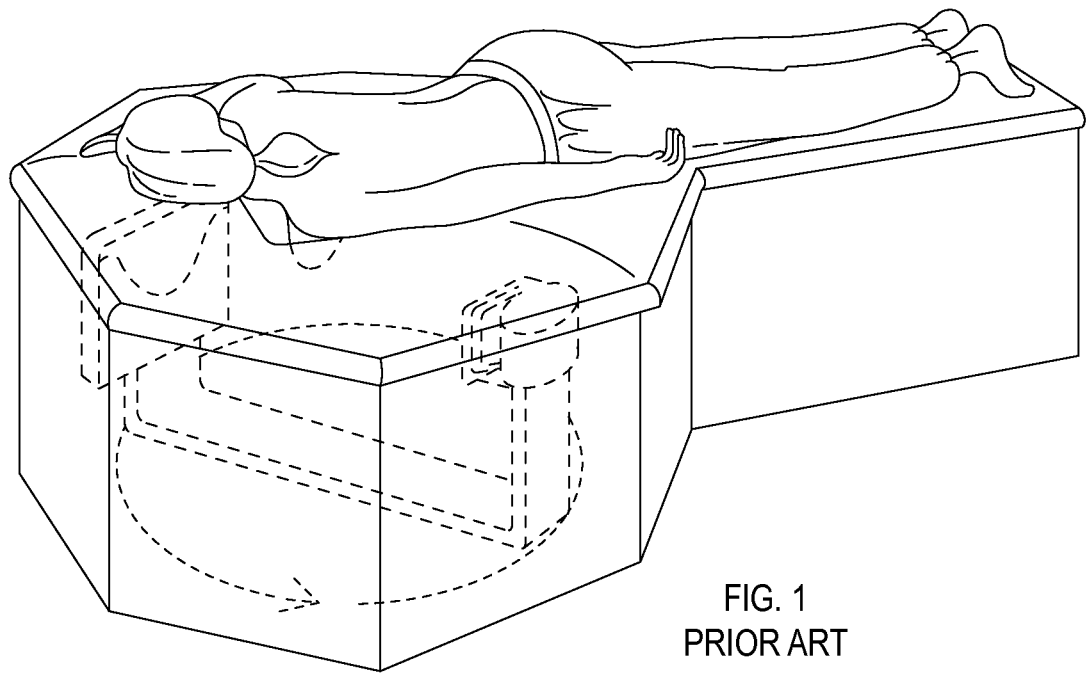
FIG. 1 illustrates a conventional imaging apparatus including a single C-arm supporting an X-ray tube and an imager.
Figure 2:
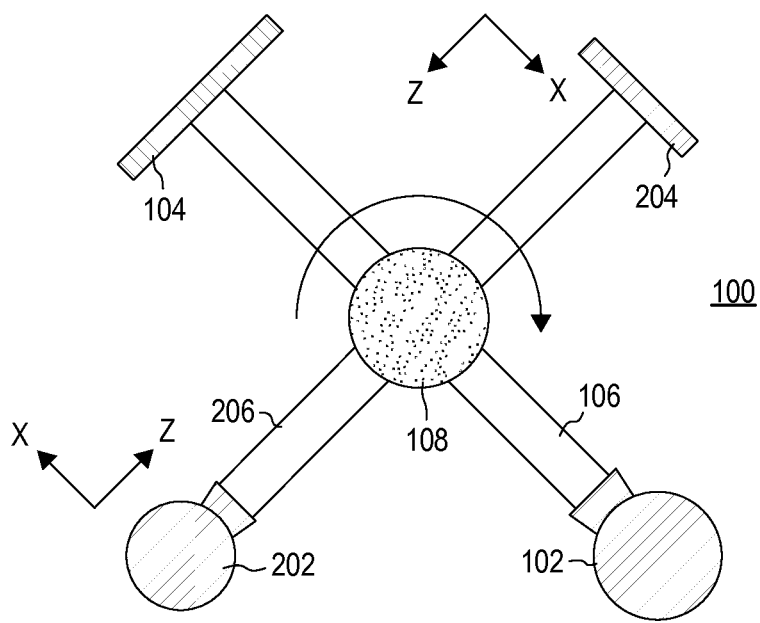
FIG. 2 illustrates an exemplary radiation apparatus in accordance with some embodiments of the invention.

FIG. 2 illustrates an exemplary radiation system 100 that can embody the principle of the invention. The radiation system 100 includes a first radiation source 102 and a first detector 104 positioned opposite to each other. The first radiation source 102 and first detector 104 may be supported at the opposite sides of a support structure such as a first C-arm, gantry or the like 106. The radiation system 100 may include a second radiation source 202 and a second detector 204 positioned opposite to each other. The second radiation source 202 and second detector 204 may be supported at the opposite sides of a support structure such as a second C-arm, gantry or the like 206. A panel or structure (not shown in FIG. 2) supports a body to be irradiated in a position such as supporting a patient in a prone, supine, upright, or any other suitable positions. The support structure may be provided with an opening configured to allow a body portion such as a patient's breast 108 to pass through to be exposed to at least a portion of radiation beams from the first and second radiation sources 102, 202. In some embodiments the support structure may be a part of an enclosure which encloses the first source 102 and detector 104 and the second source 202 and detector 204. The first and second C-arms or gantries 106, 206 may be coupled to a shaft or rotatable about a same axis. The shaft may be operable to be moved by a mechanism including such as motors. By way of example, the system 100 may be configured to irradiate a prone or supine patient's breast and the shaft may rotate causing the first and second C-arms 106, 206 to rotate about the prone or supine patient's breast. The prone patient may be positioned on a table or on a support panel which can be a part of an enclosure housing the radiation sources and detectors. The shaft may also move up or down to position the first radiation source 102 and detector 104 and/or the second radiation source 202 and detector 204 at a desired elevation relative to the body portion 108 to be irradiated. Alternatively, the system 100 may be configured to irradiate an upright patient's breast and the shaft may rotate causing the first and second C-arms or gantries 106, 206 to rotate about an upright patient's breast. It will be appreciated that the radiation system 100 may include three or more radiation sources of suitable spot sizes and three or more detectors of suitable pixel sizes configured for desired applications.

The first radiation source 102 may be configured to produce beams suitable for irradiating a whole breast or a portion of the breast to acquire an image data set in a short period of time. Various X-ray sources are known and their detail constructions are not described herein. In general, an X-ray source may include a cathode and an anode enclosed in a vacuum envelope. The cathode includes a filament or filaments in a focusing cup configured to generate electrons when a voltage is supplied to the filament. The anode supports a target or targets configured to produce X-ray photons when impinged by electrons. In use, a voltage is applied to the cathode to generate a cloud of electrons. Because of the potential between the anode and cathode, the electrons accelerate toward the anode forming a beam of electrons striking the target on the anode. The electrons excite the target atoms into high energy states. As the excited atoms relax back to the ground states, a small fraction of this excitation energy is emitted from the target surface in the form of X-ray photons. The emission shape has a somewhat Gaussian intensity profile with a width (half maximum value of the emission profile). This width of the emission profile is referred to as X-ray spot size as used herein. The X-ray spot size is somewhat wider than the width of the electron beam, which can be controlled by various means including such as by varying the size and configuration of the filament and focusing cup, or the length of the tube etc. A variety of X-ray sources or tubes are commercially available e.g. from Varian Medical Systems, Inc. in Palo Alto, Calif. or from other manufacturers. In some embodiments, the first radiation source may be chosen to have relatively large spot size such as ranging from 0.1 to 5.0 mm. An X-ray source with a large spot size generally provides more X-ray power output, which means that it takes a shorter period of time to acquire a projection image of a given quality (signal-to-noise ratio).

The second radiation source 204 may be configured to image an identified region of interest of reduced volume to acquire an image data set with higher resolutions. The region of interest may be small cancerous lesions of the size on the order of microns or submicrons or microcalcifications in the breast tissue. As will be described in greater detail below, a radiation source with a small spot size is desirable in acquiring image data sets resolving reduced volumes. The second radiation source 202 may have a spot size ranging from 0.1 to 300 microns. In some embodiments, the second radiation source 202 may be a microfocus X-ray tube having a focus spot size ranging from 0.5 to 10 microns. In some embodiments, X-ray tubes with submicron spot sizes may be used as the second radiation source 202.

The first and second radiation sources 102, 202 may include beam shaping devices to provide fan beams or cone beams for cone beam computed tomography (CBCT) or digital tomography (CBDT). In some embodiments, the cone beam may be collimated or sliced in shape so that the patient's breast is exposed but the heart, lungs or other healthy tissue are not directly in the beam path.

The first detector 104 may be configured to acquire an image data set for a whole breast or a portion of the breast in a short period of time. The second detector 204 may be configured to acquire an image data set for suspect regions of interest with high resolutions. In some embodiments, the first detector 104 has a large active detection area to receive radiation passing through the whole breast or through a large portion of the breast. In some embodiments, the second detector 204 may have a small active detection area but include imaging elements with a small pixel size to provide high spatial resolution. Various detectors are known and their detail construction is not described herein. In general, the first and second detectors 104, 204 may include a radiation conversion layer and a detector array. The radiation conversion layer may include scintillators configured to generate light photons in response to X-ray radiation. The detector array may include a plurality of photo detector elements configured to generate electrical signals in response to the light photons from the radiation conversion layer. Alternatively, the radiation conversion layer may include photoconductors configured to generate electron-hole pairs or charges in response to X-ray radiation, and the detector array includes a plurality of detector elements configured to collect the charges and generate electric signals in response to the charges. Various other detection schemes are possible and can be used. The detector array may be pixilated forming a plurality of imaging elements (pixels). The imaging elements may arrange in rows or columns or other patterns forming an active detection area. Each of the imaging elements or pixels may have a cross sectional dimension or size (pixel size).

By way of example, for an X-ray imager having a 40×30 cm active detection area, a total of 3.1 million individual pixels may be arranged in 1536 rows and 2048 columns with each square pixel measuring 194 microns on a side. For an X-ray imager having a 5×5 cm active detection area, a total of 1.05 million individual pixels may be arranged in 1024 rows and 1024 columns with each square pixel measuring 50 microns on a side. It should be noted that the specific examples are provided for illustration purpose only and are not intended to limit the claimed invention. Depending on the requirements for a particular application, a different detection area may be divided into a different number of rows and columns to provide for a different number of total pixels with different pixel sizes. The image data from the image elements can be read out one line at a time. Alternatively, the image data from a plurality of lines of the image elements can be read out simultaneously. Various arrangements are known to reduce the time it takes to readout signals from the image elements, and thus improving a frame rate of the imager, or the number of frames that can be generated by the imager per second.

In an exemplary embodiment, the first detector 104 is an X-ray imager having an active detection area with 20-50 cm on a side and imaging elements with a pixel size ranging from 100 to 200 microns on a side. The first radiation source 102 is an X-ray source having a spot size ranging from 0.5 to 3 mm. The distance between the first radiation source 102 spot location and a location on the surface of the first detector 104 is about 1-1.5 m. The second detector 204 is an X-ray imager having an active detection area of 5-10 cm on a side and imaging elements with a pixel size ranging from 0.5 to 100 microns on a side. The second radiation source 202 is an X-ray source having a spot size ranging from 0.1 to 200 microns.

In some embodiments, the second radiation source 202 and/or second detector 204 may be movable relative to the body portion 108 to be imaged. For example, the second radiation source 202 and/or second detector 204 may be moved longitudinally to be closer to or farther away from the body portion 108 (z direction), or moved laterally to have different angles with respect to the body portion (x direction, and y direction perpendicular to the x-z plane). As described above, the second radiation source 202 may have a small spot size and the second detector 204 may have a small active detection area and/or have imaging elements with a small pixel size adapted to image a region of interest of a reduced volume such as microcalcifications or small cancerous lesions within a patient's breast. The capability of moving the second radiation source 202 and/or second detector 204 in one or more directions allows proper positioning and/or alignment of the source and the detector with respect to the small region of interest, and allow the use of magnification techniques in imaging. For example, the distance between the second radiation source 202 and second detector 204, or the distance between the region of interest and the source 202 or the detector 204 may be adjusted by moving the source 202 and/or the detector 204 using various mechanisms such as motors, stages, and guides etc. to provide for a proper magnification ratio. As used herein, a magnification ratio refers to a ratio of the distance from a radiation source to the detector to the distance from the radiation source to the body irradiated. For a small magnification ratio approaching to 1 e.g. when an irradiated body portion is placed directly on the detector, the spatial resolution is largely determined by the pixel size of the imaging elements of the detector. For a great magnification ratio e.g. when a breast is placed next to the radiation source, the spatial resolution is largely determined by the spot size of the radiation source. For magnification ratio values in between, the spatial resolution is largely determined by the combination of the pixel size of the detector and the spot size of the radiation source, among other factors. According to the embodiments of the invention, a desired magnification ratio may be readily obtained by adjusting the position of the second radiation source 202 and second detector 204.

The radiation system 100 may include a control (not shown in FIG. 2) to control the operation of the radiation system. For example, the control may provide power and timing signals to the radiation sources 102, 202, control image signal or data readout from the detectors 104, 204, control rotation or movement of the C-arms 106, 206, and control the positioning and/or alignment of the radiation source 202 and detector 204 etc. The control may include a memory to store various programs for the operation of the radiation system and image data acquired, and a processor such as a digital signal processor (DSP), a central processing unit (CPU), or a microprocessor (μP) to execute the programs, process or reconstruct image data acquired, or generate signals for operation of the sources and detectors, etc. The radiation system 100 may also include various feedback devices providing feedback including position and motion speed of the sources and detectors etc. The control may be configured to receive feedback signals and generate commands in response thereto.

In operation, the first radiation source 102 is caused to project a beam of radiation such as a cone beam or fan beam to a body portion such as the breast or a portion of the breast 108 which absorbs or attenuates the radiation beam to the extent dependent on the density of the body portion. Radiation passing through the body portion 108 is received by the first detector 104, which converts the received radiation to electrical signals or image data. The first radiation source 102 and the first detector 104 may be caused to make one or more 360 degree rotations around the body portion 108 during the image data acquisition. Alternatively, the first radiation source 102 and the first detector 104 may make a rotation less than 360 degrees such as 180 degrees plus the angle of the beam pattern. Other angles of rotation may also be used. Multiple projection images may be taken from various angles to acquire an image data set for the body portion. Generally 500 to 600 projection images may be taken from various angles to form a full cone beam CT data set. Alternatively, fewer projection images from limited angles may be taken to form a digital tomosynthesis image data set.

In some embodiments, the first radiation source 102 and the first detector 104 may be configured to generate an image data set for the body portion 108 in short period of time. As described above, the first radiation source 102 may have a large X-ray spot size to provide high X-ray power output to aid in fast image acquisition. The first detector 104 may be a digital imager having imaging elements with a pixel size, pixel number, and/or signal readout electronics etc. that are configured to generate projection images at high frame rates. By way of example, a CBCT or CBDT image data set may be acquired in 5 seconds or less, or 1 second or less. In some embodiments, an image data set may be acquired in 35 milliseconds or less. In some embodiments, an image data set may be acquired in 0.1 milliseconds or less.

In some embodiments, a contrast enhanced agent may be administered to the body portion before using the first radiation source 102 and first detector 104 to acquire an image data set. Various contrast agents are known and their effective amount are dependent on the location of the body portion being imaged, the location of the administration site, the size, weight, and the physical condition of the patient etc. There should be a time delay between the administration of the contrast agent and the image acquisition depending on the lesion type, size and the individual patient's characteristics such as cardiac output. By way of example, in some embodiments where a patient's breast is examined, a total of 100 ml of a contrast agent may be injected into the patient's brachial vein at 4 ml per second for 25 seconds, and imaging commences 140 seconds after the injection of the contrast agent. In some embodiments, image acquisition may start approximately 40 to 150 seconds after the injection of a contrast agent into the patient's vein in the amount of 50-150 ml.

The projection images may be processed or reconstructed to produce two or three dimensional images of the body portion using techniques known in the art including backprojection reconstruction techniques. For example, reconstructed coronal or sagittal images of the whole breast may be generated for a desired cross section of the body portion, thus removing interference of the layers before or after the particular cross section. The reconstructed images are viewed and analyzed using various techniques, and one or more suspect regions of interest may be identified that need be further investigated to confirm whether the suspect regions are cancerous.

The second radiation source 202 and second detector 204 are positioned or aligned with respect to the identified suspect region of interest by moving the source 202 and/or detector 204 in one or more directions. The distance between the second radiation source 202 and second detector 204, or the distance between the region of interest and the source 202 or the detector 204 may be adjusted by moving the source 202 and/or the detector 204 to provide for a proper magnification ratio. Similar to the image data acquisition for the whole breast or a portion of the breast using the first radiation source 102 and first detector 104, the second radiation source 202 and second detector 204 may be caused to make one or more 360 degree rotations during image data acquisition for the suspect region of interest. Alternatively, the second radiation source 202 and second detector 204 may make a rotation less than 360 degrees such as 180 degrees plus the angle of the beam pattern. Other angles of rotation may also be used. To save dose, a single projection image may be acquired for the suspect region of interest. A single projection image may be sufficient since superposition of imaging layers does not seem to be a major problem in image resolution of microcalcifications. In some embodiments, the second radiation source and detector are caused to rotate about a same axis as the first radiation source and detector in image acquisition. For example, both the first source and detector and the second source and detector may be caused to rotate about a vertical axis or a horizontal axis in image acquisition.

The projection images acquired by the second radiation source 202 and second detector 204 may be processed or reconstructed to produce two or three dimensional images of the region of interest using techniques known in the art including backprojection reconstruction techniques. With higher spatial resolution, the suspect regions of interest may be viewed and analyzed in the reconstructed images whether the suspect regions are cancerous.

A radiation system and method has been described. Those skilled in the art will appreciate that various other modifications may be made within the spirit and scope of the invention. All these or other variations and modifications are contemplated by the inventors and within the scope of the invention.

What is claimed is:

1. A radiation method, comprising:
   imaging a body portion using a first X-ray source and a first X-ray detector to acquire a first image data set;
   identifying a reduced volume within the body portion containing a region of interest based on the first image data set; and
   imaging only the identified reduced volume containing the region of interest using a second X-ray source and a second X-ray detector to acquire a second image data set;
   wherein the first X-ray source and first X-ray detector and the second X-ray source and second X-ray detector are caused to rotate about a vertical axis in imaging the body portion and the reduced volume containing the region of interest
   wherein the first X-ray source has a first spot size, the first X-ray detector is a flat panel detector comprising a plurality of pixels each having a first pixel size, the second X-ray source has a second spot size, and the second X-ray detector is a flat panel detector comprising a plurality of pixels each having a second pixel size, wherein the second spot size of the second X-ray source is smaller than the first spot size of the first X-ray source and the second pixel size of each of the second pixels of the second X-ray detector is smaller than the first pixel size of each of the first pixels of the first X-ray detector.

2. The radiation method of claim 1 wherein the first image data set acquired comprises a cone beam CT image data set.

3. The radiation method of claim 1 wherein the first data set acquired comprises a digital tomosynthesis image data set.

4. The radiation method of claim 1 wherein the second image data set acquired comprises a single projection image.

5. The radiation method of claim 1 wherein said body portion is a prone patient's breast and the identified reduced volume containing the region of interest is a reduced volume in the breast.

* * * * *